United States Patent
Yao et al.

(10) Patent No.: US 7,260,489 B2
(45) Date of Patent: Aug. 21, 2007

(54) METHOD OF DISPLAYING MULTI-CHANNEL WAVEFORMS

(75) Inventors: Li Yao, Nanshan (CN); Wei Chen, Nanshan (CN)

(73) Assignee: Shenzhen Mindray Bio-Medical Electronics Co., Ltd. (CN)

( * ) Notice: Subject to any disclaimer, the term of this patent is extended or adjusted under 35 U.S.C. 154(b) by 0 days.

(21) Appl. No.: 11/316,182

(22) Filed: Dec. 22, 2005

(65) Prior Publication Data

US 2006/0161360 A1 Jul. 20, 2006

(30) Foreign Application Priority Data

Jan. 18, 2005 (CN) .......................... 2005 1 0032882

(51) Int. Cl.
*G01R 13/02* (2006.01)
(52) U.S. Cl. ........................................................ 702/67
(58) Field of Classification Search .................. 702/67; 379/88.01; 345/534
See application file for complete search history.

(56) References Cited

U.S. PATENT DOCUMENTS

| | | | |
|---|---|---|---|
| 4,132,928 A | | 1/1979 | Berlin |
| 4,257,043 A | * | 3/1981 | Tsuchiko ..................... 345/534 |
| 5,579,010 A | | 11/1996 | Iihoshi et al. |
| 5,859,898 A | * | 1/1999 | Checco ..................... 379/88.01 |
| 5,960,081 A | | 9/1999 | Vynne et al. |
| 2003/0208328 A1 | * | 11/2003 | Pickerd ........................ 702/67 |

FOREIGN PATENT DOCUMENTS

| | | |
|---|---|---|
| CN | 1584606 | 2/2005 |
| GB | 2103459 | 2/1983 |
| GB | 2133164 | 7/1984 |
| JP | 7-260827 | 10/1995 |
| JP | 10-82803 | 3/1998 |
| JP | 2001-257610 | 9/2001 |

* cited by examiner

*Primary Examiner*—Bryan Bui
*Assistant Examiner*—Xiuqin Sun
(74) *Attorney, Agent, or Firm*—McDonnell Boehnen Hulbert & Berghoff LLP

(57) ABSTRACT

A method of displaying multi-channel waveforms including the steps of: dividing at least one waveform screen in a video memory which is mapped to a display terminal into a plurality of waveform windows, wherein boundaries of each of the windows are defined by a plurality of values set in at least a set of boundary registers; establishing a waveform parameter table in a system memory; writing waveform data into a logical space in the waveform screen corresponding to a waveform by writing operations from CPU to the video memory; and based on parameters of the waveform windows in the waveform parameter table, performing a display mode defined by the parameter by means of changing the mapping relationship between the video memory and the display terminal, before transmitting the data of each of the waveform windows read out from the video memory to the display terminal.

11 Claims, 3 Drawing Sheets

| | | |
|---|---|---|
| | xo | |
| | xro | parameters of |
| S H | y_end | the 1st channel of waveforms |
| other | | |
| | xo | |
| | xro | parameters of |
| S H | y_end | the 2nd channel of waveforms |
| other | | |
| | xo | |
| | xro | parameters of |
| S H | y_end | the 3rd channel of waveforms |
| other | | |
| | xo | |
| | xro | parameters of |
| S H | y_end | the 4th channel of waveforms |
| other | | |
| ⋮ | | |
| | xo | |
| | xro | parameters of |
| S H | y_end | the nth channel of waveforms |
| other | | |

FIG. 6

METHOD OF DISPLAYING MULTI-CHANNEL WAVEFORMS

BACKGROUND OF THE INVENTION

The present invention generally relates to a technique for displaying in a field of image communication, particularly to a method of displaying multi-channel waveforms in embedded systems.

A medical patient monitor is typically an embedded system, which is necessary to support displaying multi-channel waveforms. In such system, physiological signals of a human body, such as ECG (electrocardiograph), SPO2 (Pulse Oxygen Saturation) and NIBP (non-invasive blood pressure) and so on, are measured by sensors and detection circuit, then physiological parameter values are obtained which will be recorded in waveform after being subjected to a calculation process, and finally displayed in real time on display terminals such as CRT (cathode-ray tube) and LCD (Liquid Crystal Display). In general, display terminals of patient monitors are required of supporting high-resolution (above 640*480) color displaying and employing display interfaces with special styles, e.g., displaying values and waveforms of various physiological parameters and text information of menu, alert and help in a plurality of colors under black background. Specially, the waveforms should be displayed dynamically by means of refreshing, scrolling and parallel dual-channel display. The refreshing refers to redrawing the display of waveform point-by-point from left to right, and automatically returning to the leftmost end from the rightmost end to continue redrawing. The scrolling refers to moving the whole waveform from right to left, and moving a new portion of the waveform in from the right end of the display region while moving an old part out of the left end. The parallel dual-channel display refers to displaying two waveforms of the left and right channels, which locate at the left and right parts of screen respectively, in parallel by means of refreshing and scrolling in a same horizontal region.

In a system using techniques for displaying, pixel array information on display screen is generally stored in a video memory in order to improve availability ratio of CPU (central processing unit) and main memory. The principle of the above technique is mainly to map the display terminal to a two-dimensional array, wherein each pixel is mapped to one element of the two-dimensional array, the value of the element is a color code of a corresponding pixel, and the y-coordinate and x-coordinate of the pixel are two subscripts in the two-dimensional array. In particulars, the pixel with a coordinate (x, y) on the display terminal is mapped to the element A (x, y) in the two-dimensional array. The video memory is used as a physical device for storing the two-dimensional array such that writing a data to the video memory via CPU corresponds to drawing a point on the display device. Data for display in the video memory may be automatically read out and displayed at appropriate positions on the display device by a display drive circuit.

Like most of embedded systems, patient monitors employ two kinds of methods to drive display device. One method is to display various character information and waveform by a general display control chip in accordance with a common graphics displaying method. In details, all of the data for display including characters and waveforms are calculated and written into the video memory by main CPU; and the data for display in the video memory are read out and transmitted to the display terminal to display a corresponding character and waveform by the general display control chip. With this method, when a waveform is scrolled, it is necessary for CPU to erase the whole waveform being displayed and overwrite all of the refreshed waveform data to the video memory so as to perform the moving of the waveform, thus leading a very heavy load of CPU. In a case of displaying multi-channel waveforms simultaneously, expenses of software in the system will be significantly increased so that the whole performance of the system is degraded. Consequently, this method has no advantage in efficiency despite of high cost.

The other method is to implement a dedicated display drive circuit by FPGA (field programmable gate array). With this method, special display mode such as scrolling of signal waveforms could be realized by hardware acceleration, thereby the load of CPU may be greatly relieved.

The cost of the system using this method is low, while the efficiency is rather higher. in the principle of the method, when a waveform in a horizontal region within a coordinate range of y1<y<y2 is to be scrolled, a mapping rule of the video memory is changed such that A ((x+xo) mod X, y) in the video memory is mapped to (x, y) on the display terminal, wherein xo represents an offset and X represents the number of horizontal pixels. As a result of the mapping, the waveform being displayed in the region is moved left for xo points in horizontal direction and the waveform which has been moved out of the display region (i.e., moved left to a point with a negative abscissa ) is retraced to the right side of the display region. In this way, the scrolling of a waveform could be performed without refreshing the whole of the two-dimensional array so long as the value of xo is changed at a certain rate by the system. For the convenience of the following description, a circuit for display in FPGA is referred as display logic.

In accordance with this method, in order to realize half-screen display of dual-channel waveforms in a region with a coordinate range of y1<y<y2, it is required of two offsets xo, each of which corresponds to each scrolling waveform. In a case that the waveforms of the two channels are arranged horizontally in the left and right screens respectively, display logic should determine the display region of each waveform so as to apply different offsets to different regions. In the following description, the behavior of applying different offsets to different regions is referred as switching of waveform parameters.

There are two aspects of defects in the above-mentioned prior art. One aspect lies in that more logic resources will be needed with the increase of waveforms. Taking an example of a resolution of 1024*768 in the technique of parallel dual-channel display, 10 bits are required for each of the offsets 1xo and rxo of the left and right waveform as well as y2 which represents the lower boundary of the display region. Thus 30 registers in FPGA are required per dual-channel waveforms to store waveform parameters. If more waveforms are desired to be displayed in each of the horizontal regions, larger capacity of registers will be required with more channels of waveforms. The other aspect lies in degradation of the performance of the chip for display with the increase of channels of waveforms, because the system usually requires higher display resolution to cope with the increase of the waveforms, which means that the highest operation frequency of the chip for display should be improved. In accordance with this method, however, MUX (multiplexer) should be used in FPGA to perform the switching of the waveform parameters. If the number of inputs of MUX is large, the switching delay will be considerably large, resulting in degradation of the highest operation frequency of the chip for display. Consequently, it is difficult for existing solution to support such a display where waveforms of more than 7 channels are scrolled simultaneously. Furthermore, there is no solution provided in the prior art for the display of multi-channel waveforms in a same region in parallel.

BRIEF SUMMARY OF THE INVENTION

The present invention is directed to provide a method of displaying multi-channel dynamical waveforms on a display device simultaneously at a high efficiency with a low cost for embedded system, in order to solve the inconsistency between the increase of waveforms and the resultant significant increase of logic resources and degradation of the performance of chips for display, enabling an excellent extensibility of the system.

Accordingly, the present invention is conceived according to the following conception. In a system in which a control circuit is implemented by FPGA or ASIC (application specific integrated circuit), waveforms under changes and text and interface information under relatively few changes are processed separately so as to improve the efficiency of displaying. Further, information of a waveform screen which contains multi-channel waveforms under changes may be processed with the waveform screen being divided into multiple waveform screens, which enable dynamic display of the multi-channel waveforms in parallel in a same region on the display terminal. In order to refresh or scroll in different rate the multi-channel waveforms under changes respectively in different horizontal regions and in different windows of a same horizontal region in a same waveform screen independently, the system establishes a parameter table in a memory for the waveform screen to define parameters of waveforms of each channel, such as display mode, boundary of a window and so on, so that waveforms of each channel may have different boundaries and different rates of refreshing and scrolling, resulting in increased flexibility of the arrangement of waveforms. Furthermore, switching delay resulted in the switching of waveform parameters may be significantly lowered by means of the parameter table in the memory rather than by means of MUX, thereby dynamic display of the multi-channel waveforms could be realized at a high efficiency with a low cost, meanwhile the extensibility of the system may be improved.

As a first technical solution under the conceiving of the present invention, a method of displaying multi-channel waveforms is proposed, which is used for displaying text information and multi-channel waveforms simultaneously for embedded systems, the method comprising the steps of:

a. assigning a plurality of separate spaces in a video memory, each of which is mapped to a same display terminal, wherein at least one of the spaces is named as a waveform screen which is used for storing waveform data; and dividing writing operations for a video memory by CPU, wherein writing operations for a video memory divided by CPU contains at least a writing operation for the waveform screen;

b. transmitting data including the waveform screen data which is read out from the video memory to corresponding ones of processing channels to be processed respectively by a display drive circuit, wherein the channels contains channels for waveform screen data which are named as waveform channels; and c. synthesizing multi-channel data processed in and output from the corresponding channels, and transmitting the synthesized data to the display terminal.

According to the technical solution above mentioned, in the step a, at least one of the remaining spaces is used for storing character data which is named as a character screen, and writing operations for a video memory divided by CPU further contains writing operations for the character screen accordingly; in the step b, each of the character screen data and each of the waveform screen data which are read out from the video memory are transmitted to corresponding ones of character screen channels and waveform screen channels to be processed respectively; and in the step c, multi-channel data processed in and output from the corresponding character screen channels and waveform screen channels is synthesized, then transmitted to the display terminal. The multi-channel waveforms may be processed in each of the waveform screen channels in such a way that each waveform is displayed in different modes. And according to the technical solution above mentioned, the synthesis of the multi-channel data processed in and output from the corresponding character screen channels and waveform screen channels may be performed by covering the waveform data with the character information data or covering the character information data with the waveform data. Color information contained in each of the waveform data of the plurality of waveform screens which is mapped to a same region of the display terminal and displayed in parallel thereon is different from each other.

According to the technical solution above mentioned, the system will be advantageous in that the efficiency of processing the display of multi-channel waveforms can be improved and an excellent extensibility can be achieved.

As a second technical solution under the conceiving of the present invention, a method of displaying multi-channel waveforms is proposed, which is used for displaying multi-channel waveforms simultaneously in embedded systems, the method comprising the steps of:

a. dividing a waveform screen in a video memory which is mapped to a display terminal into a plurality of waveform windows arranged in a vertical direction, each of which displays a waveform or displays multi-channel waveforms in parallel in a horizontal direction respectively, wherein boundaries of each of the windows are defined by a plurality of values set in at least a set of boundary registers;

b. establishing a waveform parameter table in a memory of the system, which contains characteristic parameters of each waveform in each of the waveform windows, wherein the characteristic parameters contain at least a parameter indicating a display mode of the waveform;

c. writing waveform data into a logical space in the waveform screen corresponding to the waveform by writing operations from CPU to the video memory; and d. on a basis of the parameters of the waveform windows in the waveform parameter table, performing a display mode defined by the parameter by means of changing the mapping relationship between the video memory and the display terminal, before transmitting the data of each of the waveform windows read out from the video memory to the display terminal by a display drive circuit.

According to the second technical solution above mentioned, the contents set in the boundary register are used either to set a common boundary for all of the waveform windows, or to divide each of the waveform windows separately and set the boundary thereof, and the characteristic parameters of waveforms contain at least a vertical boundary of the waveform window. Contents set in the boundary register are also used to set a segment of horizontal region for displaying each waveform when multi-channel waveforms are horizontally displayed in the windows in parallel. The characteristic parameters of waveforms further contain a horizontal initial position xo for displaying the waveform.

According to the second technical solution above mentioned, the waveform parameter table does not occupy register resources in FPGA, so the inconsistency between the increase of waveforms and the resultant significant increase of logic resources and degradation of the performance of chips for display could be relieved, enabling an excellent extensibility and high efficiency of the system in terms of the display of multi-channel waveforms.

BRIEF DESCRIPTION OF THE DRAWINGS

FIG. 6 is a schematic diagram showing the configuration of a memory.

DETAILED DESCRIPTION OF THE INVENTION

For better understanding of the present invention, preferable embodiments of the present invention will be described below with reference to the attached drawings.

Figure 1:
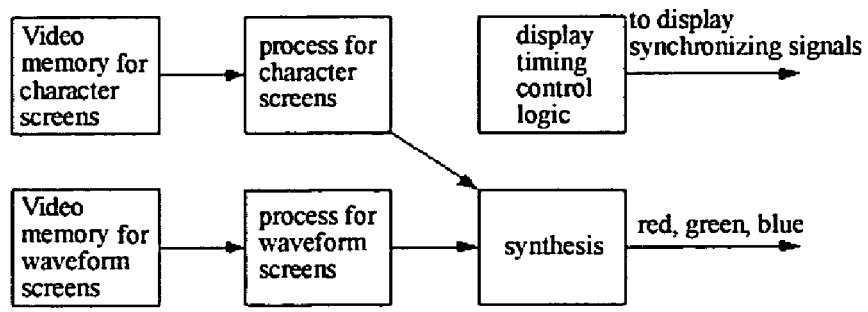
FIG. 1 is a block diagram illustrating the operation principle of the devices according to the present invention.

Taking into account of the characteristics that text information such as menus, alert, help and so on are usually required for an embedded system, the basic configuration of a display drive circuiting according to the present invention is shown in FIG. 1, which is capable of improving the efficiency of the system in terms of processing the display of multi-channel waveforms. For the reason of different requirements for dynamical display of waveforms and relatively stationary display of text information, character information and waveforms displayed physically on the same display terminal may be defined as a character screen and a waveform screen that are separated logically. That is, separate spaces may be assigned in a video memory for storing character data and waveform data respectively, accordingly writing operations for the video memory by CPU are divided into writing operation for the character screen and writing operation for the waveform screen. In this way, the character screen and the waveform screen may be processed in different manners in the system. In particulars, the character screen data and waveform screen data read out from the video memory may be transmitted to corresponding ones of character channels and waveform channels by the display drive circuit to be processed respectively; then the dual-channel data processed in and output from the character screen channel and waveform screen channel is synthesized and further transmitted to the display terminal under the control of a display timing control logic. Thereafter, in accordance with the prior art, a display logic will output different synchronizing signals for display which are corresponding to different display terminals, and display resultant synthesized display data, which will not be described in details herein any more.

Taking a system with a display resolution of 1024*768 for example, two two-dimensional arrays with 1024*768 bytes may be defined for storing character screen data (array C) and waveform screen data (array W). As for the manner of processing the character screen, C(x, y) may be mapped directly to (x, y) of the display terminal, and in special case, may be is subjected to necessary process in the character screen channel in advance. On the other hand, the multi-channel waveforms may be processed additionally in the waveform screen channel so as to display waveforms of each channel dynamically in different modes. With regard to the synthesis of the data processed in and output from the two channels, it may be defined flexibly as per practical applicability. In particulars, the waveform data may be covered by the character information data or the character information data may be covered by the waveform data. For example, waveforms of physiological signals are usually displayed in the center of a screen of a patient monitor, whereas, when a user operates the device, the waveforms of physical signals may be covered with a pop-up menu at a position where overlay occurs.

Especially, on the basis of the above processes, when multi-channel waveforms are desired to be displayed in different colors in a certain region of the display terminal, and the multi-channel waveforms are required to be displayed in different display modes or displayed dynamically at different rates, a plurality of separate spaces (waveform screens) may be set in the video memory, which are mapped to the same display terminal or a certain region of the display terminal. Each of the waveform screens stores at least one channel of waveform data, and color information contained in each of the waveform data of the waveform screens which is mapped to the same region of the display terminal is different from each other. In this way, after the multi-channel waveforms have been processed to be displayed in different modes by each of the waveform screens, the data output from each of the waveform screens may be synthesized and transmitted to the display terminal so as to enable the multi-channel waveforms to be displayed in parallel in different color in the same region by the display drive circuit. Thereby, by means of overlapping different display regions for waveforms, more waveform information may be displayed in the system.

In connection to the dynamical displaying of waveforms in an embedded system, the present invention is advantageous in that providing a method of displaying multi-channel waveforms on the basis of the processing of each of the waveform screen data, which is used for displaying multi-channel waveforms simultaneously in the embedded system, the method comprising the steps of:

a. dividing a waveform screen in a video memory which is mapped to a display terminal into a plurality of waveform windows arranged in a vertical direction, each of which displays a waveform or displays multi-channel waveforms in parallel in a horizontal direction respectively, wherein boundaries of each of the windows are defined by a plurality of values set in at least a set of boundary registers;

b. establishing a waveform parameter table in a memory of the system, which contains characteristic parameters of each waveform in each of the waveform windows, wherein the characteristic parameters contain at least a display mode of the waveform;

c. writing waveform data into a logical space in the waveform screen corresponding to the waveform by writing operations from CPU to the video memory; and d. on the basis of the parameters of the waveform windows in the waveform parameter table, performing a display mode defined by the parameter by means of changing the mapping relationship between the video memory and the display terminal, before transmitting the data of each of the waveform windows read out from the video memory to the display terminal by a display drive circuit.

Figure 4:
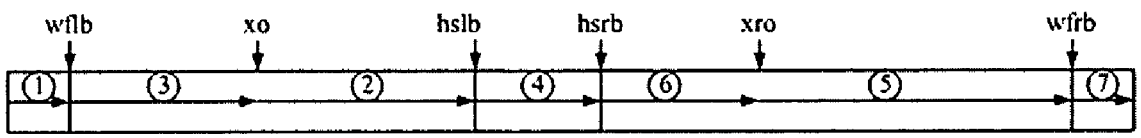
FIG. 4 is a schematic diagram showing the reading order of waveform data in a video memory in a parallel dual-channel mode.
Figure 5:
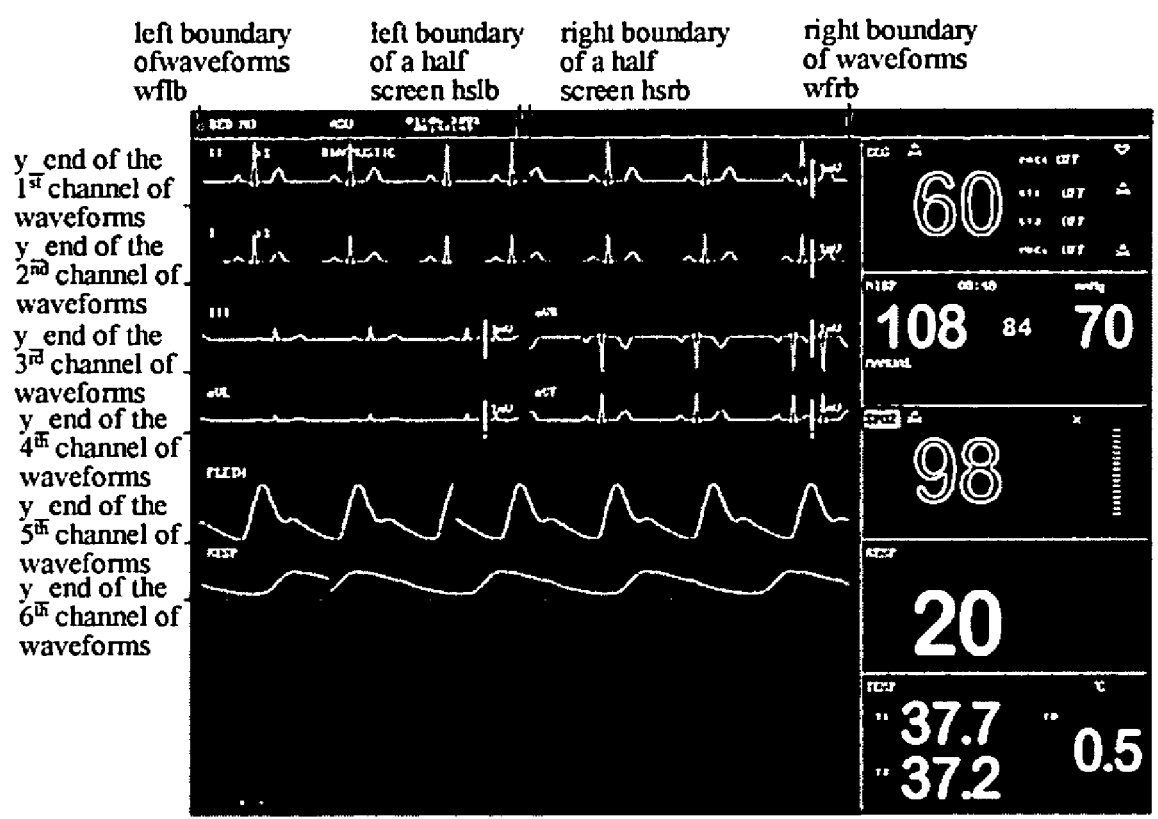
FIG. 5 is a diagram showing a practical effect of each waveform displayed on a display terminal.

Also take a system with display resolution of 1024*768 with 256 colors which is capable of displaying 32 channels of waveforms for example. Waveform data in the video memory resides in a two-dimensional array with 1024*768 bytes, which is named as a waveform screen. The waveform screen is divided into 32 waveform windows arranged in a vertical direction, each of which displays one waveform or displays horizontally multi-channel waveforms in parallel. Herein we take two channels of waveforms displayed in left and right respectively for example. As shown in Table 1, the left and right boundaries for single or parallel dual-channel waveforms which are common to all of the waveform windows are set by a set of boundary registers. Contents of the four 16-bit boundary registers may be set by software, and the boundary registers divide the display terminal as shown in FIG. 5. In Table 1, wflb and wfrb define the regions on the left and right sides of the waveform screen, which are not scrolled and correspond to the regions ① and ⑦ in the waveform screen of the video memory in FIG. 4; and hslb and hsrb define the "gap" between the left and right parallel waveforms, which is not scrolled and corresponds to the region ④ in the waveform screen of the video memory in FIG. 4. The set of boundary registers are shared by all of the waveform windows, that is, it is assumed here that the same rule for diving boundaries is applied for all of the waveforms. Needless to say, more registers may be used for assigning different boundaries for each of waveform windows and assigning segments of horizontal region for displaying each waveform when multi-channel waveforms are displayed in parallel in the window.

TABLE 1

Waveform boundary register (left/right boundary of the waveform window, and left boundary/right boundary of a half screen; 16 bits)

| Register | Description |
| --- | --- |
| wflb | left boundary of the waveform window, 0~1023 |
| wfrb | Right boundary of the waveform window, 0~1023 |
| hslb | right boundary of the left half screen |
| hsrb | left boundary of the right half screen |

The other characteristics of the waveform are defined by a waveform parameter table established in a memory in the system. As shown in Table 2, the parameter table established in RAM (random access memory) built in FPGA or RAM outside of FPGA contains definition of characteristic parameters of at least one waveform. To facilitate the function extensibility of the system, each waveform window is defined by 4 registers each with 16-bits. In Table 2, Rev represents a reserve bit; S represents a control bit for scrolling mode, wherein S=0 indicates that present window is not scrolled, i.e., displayed in refreshing mode, and S=1 indicates that present window is scrolled; and H represents a control bit for a mode of multi-channel waveforms, wherein H=0 indicates that present window displays one waveform, and H=1 indicates that present window displays two channels of waveforms at left and right sides respectively. It is assumed that the waveform windows are arranged from top to bottom in an order of serial numbers, and the characteristic parameters of the waveform also contain at least a vertical boundary of the waveform window. In Table 2, y-end represents the ordinate of the lower boundary of the waveform window. It is set in the system that the ordinate of the upper boundary of each window is the ordinate of the lower boundary of the former waveform window incremented by 1. Alternatively, the ordinate of the upper boundary of each waveform window may be set, or both of the ordinates of the upper and lower boundaries of each waveform window may be set together by the reserve bit. The characteristic parameters of the waveform also contain a horizontal initial position xo of each waveform. In parallel dual-channel mode for display with H=1, xo represents the horizontal initial position of the left waveform, and xro represents the horizontal initial position of the right waveform.

TABLE 2

A set of waveform parameters in a memory storing waveform parameters (16 bits)

| Address | 15 | 14 | 13 | 12 | 11 | 10 | 9 | 8 | 7 | 6 | 5 | 4 | 3 | 2 | 1 | 0 |
| --- | --- | --- | --- | --- | --- | --- | --- | --- | --- | --- | --- | --- | --- | --- | --- | --- |
| 0 | | | Rev | | | | | | xo: horizontal initial position of the waveform | | | | | | | |
| 1 | | | Rev | | | | | | xro: horizontal initial position of the right waveform in the parallel dual-channel mode | | | | | | | |
| 2 | S | H | Rev | | | | | | y_end: the ordinate of the lower boundary | | | | | | | |
| 3 | | | | | | | | Rev | | | | | | | | |

FIG. 5 further illustrates the definitions of the above waveform parameters. In this way, the arrangement and display manner of each waveform can be controlled by these settings in the system.

The data of at least one waveform which is desired to be displayed is written into a logical space corresponding to associated waveform window in the video memory through writing operation from CPU to the video memory. Before the data of each waveform read out from the video memory is transmitted to the display terminal by display drive circuit, the mapping relationship between corresponding waveform window and the display terminal is changed by the system according to the above parameters of the waveform, so that the waveforms may be displayed in the prescribed mode.

Figure 2:
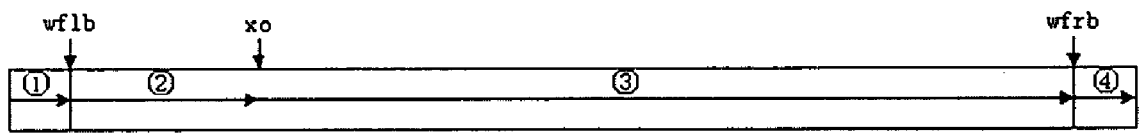
FIG. 2 is a schematic diagram showing the reading order of waveform data in a video memory in a refreshing mode.

Details of above process will be given as follows. As shown in FIG. 2, in a case of refreshing mode, waveform data is cleared and refreshed according to the value of xo which records the horizontal initial position of the waveform while xo is incremented by 1 continuously in the system in such a circulation that the overflow of wfrb will be followed by the reset of an initial value wflb, then mapped directly to the display screen by the display drive circuit, so that the display of the waveforms from left to right can be realized by means of point-by-point refreshing.

Figure 3:
FIG. 3 is a schematic diagram showing the reading order of waveform data in a video memory in a scrolling mode.

In a case of scrolling mode, some regions are specified not to be mapped to the display terminal with a horizontal offset by boundary registers; thereby some regions which are not scrolled have been assigned in the waveform window, leading to flexible arrangement of waveforms. As shown in FIG. 3, similar to the method in the refreshing mode, the waveform data is refreshed while xo is incremented by 1 continuously in a circulation in the system. The waveform data may be mapped by the display drive circuit as follows: first the region ① which is not scrolled and is applied with an address less than wflb is displayed, then the region ③ is skipped and the region ②, of which the initial address is xo, is displayed, thereafter the region ③ and the region ④ which is applied with an address larger than wfrb are displayed sequentially. In present waveform window, the mapping relationship is expressed mathematically as follows: when xo$\leq$x$\leq$wfrb, W(x, y) is mapped to (x−xo+wflb, y) on the display terminal; otherwise, when wflb$\leq$x$\leq$xo, W(x, y) is mapped to (x+wfrb−xo+1, y) on the display terminal. Therefore a horizontal offset is allowed to be applied from the logical waveform screen to the actual display screen. As xo is incremented by 1 continuously, the waveform is scrolled from right to left continuously. In embedded systems, such method of scrolling waveform in which there is a horizontal offset when the waveform screen data in the video memory is mapped to the display terminal may be realized by hardware for FPGA or ASIC, and the software of the system is merely required for refreshing the waveform data and operating the xo.

In a case that multi-channel waveforms are displayed in parallel in the windows horizontally, the multi-channel waveforms are switched from left to right while relevant steps are performed to synthesize each line of scanning data on the display terminal by the display drive circuit according to the waveform parameter table and the boundary registers of each of the multi-channel waveforms. Taking an example of a parallel dual-channel mode, two channels of waveforms are scrolled simultaneously as shown in FIG. 4. In the figure, wflb and hslb are used to set the two boundaries of the left waveform respectively, and hsrb and wfrb are used to set the two boundaries of the right waveform respectively. The regions ①-⑦ are displayed sequentially by a driving logic for display, enabling the scrolling of the two channels of waveforms in the same waveform window. If xo and xro are counted at different rates respectively, the two channels of waveforms may be scrolled at different rates. In addition, the mapping manner of any waveform may be changed, e.g., in a refreshing mode. Under such conception, the manner of displaying waveforms may be extended to be more flexible.

Furthermore, parallel dual-channel or other more complicated display mode could be realized by means of other mapping relationships between the waveform data in the video memory and the display terminal, which will not be described in details any more.

Using above method, the display terminal of the system may be supported to display at least 9 channels of waveforms dynamically in one waveform screen, and the switching of waveform parameters may be performed at ease by the above waveform parameter table in the memory. In the data structure of a parameter memory shown in FIG. 6, parameter data for controlling the first, second, third . . . channel of waveforms, each of which is composed of four units, is stored from lower address to upper address sequentially. When a frame starts to be displayed by display logic, the upper address of the waveform parameter memory is 0, and the parameters of the first channel of waveform are output via data line while the waveform is scrolled or refreshed according to the parameters of the first channel of waveform by the display logic. When line y_end has been displayed by the display logic, the upper address of the waveform parameter memory is incremented by 1, thus the parameters of the next channel of waveform will be obtained automatically. In this way, the switching of the waveform parameters could be carried out only by the change of the address of the waveform parameter memory. Since the delay between the address and data of the memory is even shorter than the delay of MUX in the prior art in a case of 7 channels of waveforms, a higher speed may be achieved in present invention.

The present invention has been experimentally tested in the medical patient monitors designed by our company. In the experiments, 32 channels of waveforms are capable of being displayed successfully only by one storage block of 4 kb (kilobit) in FPGA, which proves that the performance of the display chip is preferable than that of the prior art in a case of 7 channels of waveforms. Even the display of 64 channels of waveforms may be feasible in the technique of parallel dual-channel is display. For other devices having the similar displaying style with patient monitors, the display of more waveforms may be feasible in the technique of parallel dual-channel display or by more RAM memories with an expanded reserve bit above mentioned. However, it does not mean much for patient monitors to display more waveforms in parallel with the restriction of the resolution of the display terminal. According to present embodiment, logic resources of the system required for realizing the display of one waveform are the same with that required for realizing the display of 32 channels of waveforms, that is, it is not required of more logic resources of the system with the increase of waveforms.

In the technique of synthesizing a plurality of waveform screens aforementioned, it can be realized that a plurality of waveforms are displayed in different colors each corresponding to respective waveforms in the same display region in parallel, by means of a plurality of waveform screens in the video memory aforementioned each being mapped to the same display terminal or the same region of the display terminal, wherein color information contained in the each of the waveform data of the plurality of waveform screens which is mapped to the same region of the display terminal and displayed in parallel thereon is different from each other. As a result, the system may be extended to carry out simultaneous display of more waveforms dynamically.

Because the RAM recourses inside of FPGA or outside of the chip are used in the RAM memory above mentioned, a large amount of logic resources in FPGA may be saved, particularly in a case of inner RAM resources with a high efficiency of usage derived from high-speed access by the system. Taking the EP1C3 from Altera Company for example, a storage block of 4 kb occupies only 7.7 percent of the memory resources of the chip. Instead, even all of the 2910 logic units of the chip will not be sufficient to achieve the same function.

What is claimed is:

1. A method of displaying multi-channel waveforms, which is used for displaying multi-channel waveforms simultaneously in embedded systems, the method comprising the steps of:

a. dividing a waveform screen in a video memory that is mapped to a display terminal into a plurality of waveform windows arranged in a vertical direction, each of which displays a waveform or displays multi-channel waveforms in parallel in a horizontal direction respectively, wherein boundaries of each of the windows are defined by a plurality of values set in at least a set of boundary registers;

b. establishing a waveform parameter table in a memory of the system, which contains characteristic parameters of each waveform in each of the waveform windows, wherein the characteristic parameters contain at least a parameter indicating a display mode of the waveform;

c. writing waveform data into a logical space in the waveform screen corresponding to the waveform by writing operations from CPU to the video memory; and d. on a basis of the parameters of the waveform windows in the waveform parameter table, performing a display mode defined by the parameter by means of changing the mapping relationship between the video memory and the display terminal, before transmitting the data of each of the waveform windows read out from the video memory to the display terminal by a display drive circuit.

2. The method of displaying multi-channel waveforms according to claim 1, wherein contents set in the boundary register are used either to set a common boundary for all of the waveform windows, or to divide each of the waveform windows separately and set the boundary thereof.

3. The method of displaying multi-channel waveforms according to claim 1, wherein the contents set in the boundary register are also used to set a segment of horizontal region for displaying each waveform when multi-channel waveforms are horizontally displayed in the windows in parallel.

4. The method of displaying multi-channel waveforms according to claim 3, wherein in a case that multi-channel waveforms are displayed in parallel in the windows horizontally, the multi-channel waveforms are switched from left to right while relevant steps are performed to synthesize each line of scanning data on the display terminal by the display drive circuit according to the waveform parameter table and the boundary registers of each of the multi-channel waveforms.

5. The method of displaying multi-channel waveforms according to claim 1, wherein the characteristic parameters of waveforms further contain a parameter indicating a horizontal initial position $x_o$ for displaying the waveform.

6. The method of displaying multi-channel waveforms according to claim 5, wherein for each waveform, the steps c and d further comprises the steps of:

clearing and refreshing waveform data in the video memory according to each value of $x_o$ corresponding to the waveform in the memory for storing waveform parameters in the system while incrementing $x_o$ by 1 continuously in such a circulation that $x_o$ will be reset by a preset value wflb in a left boundary register for the waveform once it overflows a preset value wfrb in a right boundary register for the waveform; and performing different processes on a basis of different display modes, wherein in a case of refreshing mode, the waveform data in the video memory is mapped directly to the display screen by the display drive circuit, so that the display of the waveforms from left to right can be realized by means of point-by-point refreshing; and in a case of scrolling mode, the waveform data in the video memory is mapped directly to the display screen in the region outside of a waveform window by a driving logic for display, while inside of the waveform window, during the waveforms are scrolled from right to left as the continuous increment of $x_o$ by itself, a mapping relationship between the video memory and the display terminal is used by the driving logic for display, which is expressed mathematically as follows: when $x_o \leq x \leq wfrb$, $W(x, y)$ is mapped to $(x-x_o+wflb, y)$ on the display terminal; otherwise, when $wflb \leq x \leq x_o$, $W(x, y)$ is mapped to $(x+wfrb-x_o+1, y)$ on the display terminal.

7. The method of displaying multi-channel waveforms according to claim 6, wherein in a case that multi-channel waveforms are displayed in parallel in the windows horizontally, the multi-channel waveforms are switched from left to right while relevant steps are performed to synthesize each line of scanning data on the display terminal by the display drive circuit according to the waveform parameter table and the boundary registers of each of the multi-channel waveforms.

8. The method of displaying multi-channel waveforms according to claim 1, wherein the characteristic parameters of waveforms contain at least a vertical boundary of the waveform window.

9. The method of displaying multi-channel waveforms according to claim 1, wherein the waveform parameter table established in RAM built in FPGA or ASIC or in RAM memory outside of chips.

10. The method of displaying multi-channel waveforms according to claim 1, wherein the display terminal of the system is supported by the waveform screens to display at least 9 channels of waveforms dynamically.

11. The method of displaying multi-channel waveforms according to claim 1, wherein a plurality of waveform screens are included in the video memory, each of which is mapped to the same display terminal or the same region of the display terminal, wherein color information contained in the each of the waveform data of the plurality of waveform screens which is mapped to the same region of the display terminal and displayed in parallel thereon is different from each other.

* * * * *